(12) United States Patent
Peter et al.

(10) Patent No.: US 10,697,006 B2
(45) Date of Patent: Jun. 30, 2020

(54) HAIRPIN-MEDIATED AMPLIFICATION METHOD

(71) Applicant: Agilent Technologies, Inc., Santa Clara, CA (US)

(72) Inventors: Brian Jon Peter, Los Altos, CA (US); Robert A. Ach, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 142 days.

(21) Appl. No.: 15/692,215

(22) Filed: Aug. 31, 2017

(65) Prior Publication Data

US 2018/0073068 A1 Mar. 15, 2018

Related U.S. Application Data

(60) Provisional application No. 62/395,295, filed on Sep. 15, 2016.

(51) Int. Cl.
*C12P 19/34* (2006.01)
*C12Q 1/6853* (2018.01)
*C12Q 1/6806* (2018.01)

(52) U.S. Cl.
CPC ......... *C12Q 1/6853* (2013.01); *C12Q 1/6806* (2013.01)

(58) Field of Classification Search
CPC ............ C12Q 1/6853; C12Q 2521/501; C12Q 2525/151; C12Q 2525/301; C12Q 1/6806
See application file for complete search history.

(56) References Cited

U.S. PATENT DOCUMENTS

| | | | | |
|---|---|---|---|---|
| 2004/0259116 A1* | 12/2004 | Beckman | ............. | C12Q 1/6848 435/6.12 |
| 2006/0051789 A1* | 3/2006 | Kazakov | ............ | C12N 15/1093 435/6.16 |
| 2015/0197786 A1* | 7/2015 | Osborne | ............... | C12Q 1/6853 435/6.11 |

OTHER PUBLICATIONS

Kaur and Makrigiorgos, Nucleic acids research, 31(6), e26, 1-7, (Year: 2003).*
Singh et al., Molecular Biology Today, 1(3) 67-69 (Year: 2000).*

* cited by examiner

*Primary Examiner* — Cynthis B Wilder
(74) *Attorney, Agent, or Firm* — Stinson LLP

(57) ABSTRACT

In some embodiments, the amplification method may comprise producing a reaction mix comprising: a nucleic acid sample, a polymerase, nucleotides, a forward primer that hybridizes to a sequence in the bottom strand of a fragment in the sample, and a reverse primer. The reverse primer has a hairpin structure comprising a loop, a stem and a 3' overhang of at least 8 nucleotides, wherein the 3' overhang hybridizes to a sequence in the top strand of the fragment. Subjecting the reaction mix at least two rounds of denaturation, renaturation and primer extension conditions results in extension the forward and reverse primers to produce an amplification product that contains: a double stranded region comprising a nick adjacent to the 5' end of the reverse primer, and the loop of the first hairpin primer. Primer sets and kits for performing the methods are also provided.

13 Claims, 10 Drawing Sheets

HAIRPIN-MEDIATED AMPLIFICATION METHOD

CROSS-REFERENCE TO RELATED APPLICATIONS

This application claims the benefit of U.S. Provisional Patent Application No. 62/395,295, filed Sep. 15, 2016, which is incorporated by reference herein in its entirety.

BACKGROUND

Next Generation sequencing (NGS) methods typically generate millions of "reads" that originate from individual molecules of DNA. Some methods, such as nanopore sequencing methods or Pacific Biosciences SMRT technology, report sequence information from individual single molecules of DNA. However, it can be difficult to achieve suitable signal to noise ratios with single molecules, making it difficult to distinguish biological sequence changes from errors. Therefore, a number of NGS platforms such as 454, Illumina, and SOLID use a method of "clonal amplification" to generate many identical copies of individual DNA molecules. These copies are segregated in individual "clusters," or on beads, which were seeded by an individual DNA molecule. Sequencing reactions proceed on the identical copies in parallel, multiplying the signal.

Generally speaking, the clonal amplification methods fall into two classes: bead based, and surface based. Bead based methods often involve emulsion PCR, for example as commercialized by 454 and Ion Torrent technologies. Examples of surface based amplification methods include the "bridge amplification" method commercialized by Illumina and the "wildfire" or "avalanche" method described by Life Technologies. Due to technical difficulties of working with micron sized beads (clogging, enrichment of beads with DNA attached, packing uniformity), higher surface densities of amplified DNA colonies on a flow cell can generally be achieved using surface amplification methods.

Among other things, the present disclosure provides a way to amplify DNA. The method can be used to amplify DNA molecules in solution or on the surface of a support. In some embodiments, amplification may result a "cluster" of amplification products that can be sequenced by any convenient method.

SUMMARY

In some embodiments, the amplification method may comprise producing a reaction mix comprising: a nucleic acid sample, a polymerase, nucleotides, a forward primer that hybridizes to a sequence in the bottom strand of a fragment in the sample, and a reverse primer. The reverse primer has a hairpin structure comprising a loop, a stem and a 3' overhang of at least 8 nucleotides, wherein the 3' overhang hybridizes to a sequence in the top strand of the fragment. Subjecting the reaction mix at least two rounds of denaturation, renaturation and primer extension conditions results in extension of the forward and reverse primers to produce an amplification product that contains: a double stranded region comprising a nick adjacent to the 5' end of the reverse primer, and the loop of the first hairpin primer. Primer sets and kits for performing the methods are also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
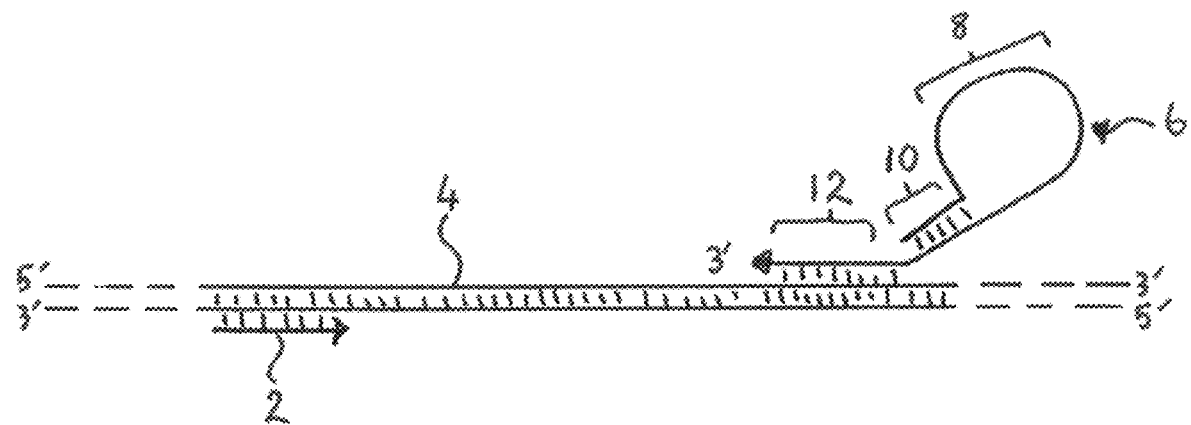
FIG. 1 schematically illustrates some features of a primer that can be used in the present method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* 3$^{rd}$ Ed., W. H. Freeman Pub., New York, N.Y. and Berg et al. (2002) *Biochemistry,* 5$^{th}$ Ed., W. H. Freeman Pub., New York, N.Y., all of which are herein incorporated in their entirety by reference for all purposes.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "nucleic acid sample," as used herein denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more then $10^4$, $10^5$, $10^6$ or $10^7$ different nucleic acid molecules. A DNA target may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "label" may include electrochemical labels, mass tags, charge blockade labels, or chromogenic labels, chemiluminescent labels, fluorescent dyes, or fluorescence quenching labels attached to the molecule of interest. Nucleotides, polynucleotides, oligonucleotides, and primers may comprise a label to aid in detection or analysis. Further examples of chemical groups that may be used as labels include chromophores, enzymes, antigens, heavy metals, magnetic probes, phosphorescent groups, radioactive materials, scattering or fluorescent nanoparticles, Raman signal generating moieties, and electrochemical detection moieties.

As used herein, the term "surface" is intended to mean a substrate or a solid support and includes any material that can serve as a solid or semi-solid foundation for attachment of capture probes, other nucleic acids and/or other polymers, including biopolymers. A surface of the invention can be modified to accommodate attachment of nucleic acids by a variety of methods well known to those skilled in the art. Exemplary types of materials comprising surfaces or solid supports include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtier plates. Specific types of exemplary plastics include acrylics, polystyrene, copolymers of styrene and other materials, polypropylene, polyethylene, polybutylene, polyurethanes and TEFLON™. Specific types of exemplary silica-based materials include silicon and various forms of modified silicon. The term "microsphere," "bead" or "particle" refers to a small discrete particle as a solid support of the invention. Populations of microspheres can be used for surface attachment of populations of capture probes. The composition of a microsphere can vary, depending for example, on the format, chemistry and/or method of attachment and/or on the method of nucleic acid synthesis. Exemplary microsphere compositions include solid supports, and chemical functionalities imparted thereto, used in polypeptide, polynucleotide and/or organic moiety synthesis. Such compositions include, for example, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and TEFLON™, as well as any other materials which can be found described in, for example, "Microsphere Detection Guide" from Bangs Laboratories, Fishers Ind. Similar to a microsphere composition, the geometry of a microsphere also can correspond to a wide variety of different forms and shapes. For example, microspheres used as solid supports of the invention can be spherical, cylindrical or any other geometrical shape and/or irregularly shaped particles. In addition, microspheres can be, for example, porous, thus increasing the surface area of the microsphere available for capture probe or other nucleic acid attachment. In addition, microspheres or beads or particles may be paramagnetic, enabling separation of the microspheres or beads or particles using a magnetic field. Exemplary sizes for microspheres used as solid supports in the methods and compositions of the invention can range from nanometers to millimeters or from about 10 nm-1 mm. Particularly useful sizes include microspheres from about 0.2 µm to about 200 µm and from about 0.5 µm to about 5 µm being particularly useful.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US 2005/0233340, which is incorporated by reference herein for disclosure of UNA.

The term "target polynucleotide," as use herein, refers to a polynucleotide of interest under study. In certain embodiments, a target polynucleotide contains one or more sequences that are of interest and under study. In certain embodiments, a target polynucleotide comprises biological sequence of interest, as well as adapter sequences.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. The 3' end of a primer may have at least 8, at least 10, at least 12 or at least 15 consecutive nucleotides of complementarity with a target sequence in a sample. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. Hybridization conditions (such as time, temperature, buffer conditions, viscosity, molecular crowding agents, concentration of the nucleic acids, addition of proteins which preferentially bind single stranded or duplex DNA, stringency) can be chosen to favor formation of certain duplexes over others, or to allow some duplexes to form while others do not. For example, short incubations or less stringent conditions may favor hybridization of duplexes with high concentrations of one or both strands (e.g., by adding a high concentration of a primer or probe, or in an intramolecular duplex formation, such as formation of a hairpin in a palindromic sequence) while longer incubations or more stringent conditions may favor formation of more stable duplexes. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to another nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together. In some cases a duplex may be formed from a single polynucleotide with self-complementary regions that can base pair.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. Many amplification reaction conditions are known in the art, and amplification of a nucleic acid may occur in aqueous solution, on a surface or solid support, in an oil-water emulsion, or in a combination of these conditions. Amplification reactions may proceed under temperature cycling or isothermal conditions. In isothermal conditions, the template strand may be separated from a complement strand by denaturing conditions (e.g., appropriate concentrations of sodium hydroxide, formamide, and the like) or by strand displacement or helicase activity provided by an enzyme. Polymerase Chain Reaction (PCR), multiple displacement amplification (MDA), strand displacement amplification (SDA), rolling circle amplification, Loop-mediated isothermal amplification (LAMP), Nucleic Acid Sequence Based Amplification (NASBA) and bridge amplification are all exemplary methods of amplification. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m = 81.5 + 16.6(\log_{10}[Na^+]) + 0.41$ (fraction G+C) − (60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to a substrate.

In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains to binding sites for sequences in the oligonucleotide.

The term "terminal nucleotide", as used herein, refers to the nucleotide at either the 5' or the 3' end of a nucleic acid strand. The nucleic acid strand may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea, formamide, or NaOH).

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, Pac Bio and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. Enzymatic conditions for polymerase extension comprising pH, concentrations of salts, ions, buffers, primers, DNA templates, and nucleotides are known in the art. If a primer that is annealed to a nucleic acid is extended, the nucleic acid acts as a template for extension reaction.

The term "barcode sequence" or "molecular barcode", as used herein, refers to a sequence of nucleotides that can be appended to a strand of a nucleic acid molecule and used to a) identify and/or track the source of a polynucleotide in a reaction and/or b) count how many times an molecule is sequenced (e.g., in cases where substantially every molecule in a sample is tagged with a different sequence, and then the sample is amplified). A barcode sequence may be at the 5'-end, the 3'-end or in the middle of a oligonucleotide sequence. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "amplification reagents" refers to all reagents that are required for performing amplification on a template. As is known in the art, for DNA amplification, such reagents essentially include at least one primer, a DNA polymerase, and nucleotides. Depending on the polymerase used, ions (e.g., $Mg^{2+}$) may also be present. PCR reagents may optionally contain a template from which a target sequence can be amplified.

As used herein, the term "flap cleavage reaction" refers to a reaction in which a substrate is cleaved in an overlap-dependent manner by a flap endonuclease to release a flap. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447).

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable.

The term "nick", as used herein, refers to the site of a missing phosphodiester bond between two adjacent nucleotides in a strand of a double-stranded DNA molecule. The nucleotides that are adjacent to the nick may contain a 3'-hydroxyl group and a 5' phosphate group, or they may contain a 3' hydroxyl group and a 5' hydroxyl group. Nicks with a 3' hydroxyl group and a 5' phosphate group may also be referred to as "ligatable nicks."

The term "adjacent to" refers to a distance of less than the longest dimension of a nucleotide. The term "ligatably adjacent to" means that two nucleotides are immediately adjacent to one another on a strand with no intervening nucleotides.

The term "non-naturally occurring" refers to a composition that does not exist in nature. Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "variant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a composition, e.g., a reaction mix, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "strand displacement" as used herein refers to an enzymatic reaction where one strand of a hybridized duplex becomes unpaired from the duplex. "Strand displacement activity" or "SD activity" refers to the enzymatic activity enabling strand displacement. For example, a DNA polymerase with strand displacement activity may be able to extend a primer into a substantially duplex template DNA, while a polymerase lacking strand displacement activity (or working under non-SD conditions) may be blocked when it encounters a duplex region downstream of the primer in the template DNA. In some cases, SD activity may be paired with another enzymatic activity, such as exonuclease activity, which may degrade the displaced strand. Non-limiting examples of strand displacement enzymes include polymerases, helicases, recombinases, and the like. Non-limiting examples of polymerases with SD activity include Bst DNA polymerase (large fragment), phi29 DNA polymerase, SD Polymerase, TopoTaq polymerase, and the like. Non-limiting examples of polymerases lacking SD activity include T4 DNA polymerase, T7 DNA Polymerase, Sulfolobus DNA Polymerase IV, Phusion DNA polymerase, and the like. "Strand displacement conditions" or "SD conditions" refer to enzymatic reaction conditions that favor strand displacement or allow strand displacement to happen. These reaction conditions may include higher or lower temperature, inclusion of a denaturant such as formamide or urea, buffer conditions, inclusion of single stranded binding proteins, inclusion of enzymes such as helicases, and the like. One enzyme may have SD activity under one set of conditions, but not at another set of conditions. For example, a particular DNA polymerase may be able to displace a strand under one set of conditions, for example, at a certain temperature, but may not be able to displace said strand a different set of conditions. Strand displacement characteristics of enzymes are known in the art, and information about strand displacement activities may also be accessed on www.neb.com. In certain cases an enzyme which is not generally known to have strand displacement activity, may be engineered to have strand displacement activity.

The term "d-loop" or "displacement loop" refers to a triple stranded DNA structure wherein two strands of a DNA duplex are held apart by a third strand of DNA which is paired to one strand of the duplex.

The term "probe", as used herein, refers to a nucleic acid that is complementary to a nucleotide sequence of interest. In certain cases, detection of a target analyte requires hybridization of a probe to a target. In certain embodiments, a probe may be immobilized on a surface of a substrate. A "substrate" can have a variety of configurations and material, e.g., a sheet, bead, glass cover slip, or other structure. In certain embodiments, a probe may be present on a surface of a planar support, e.g., in the form of an array.

An "array" includes any two-dimensional or substantially two-dimensional (as well as a three-dimensional) arrangement of spatially or optically addressable regions bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Figure 2:
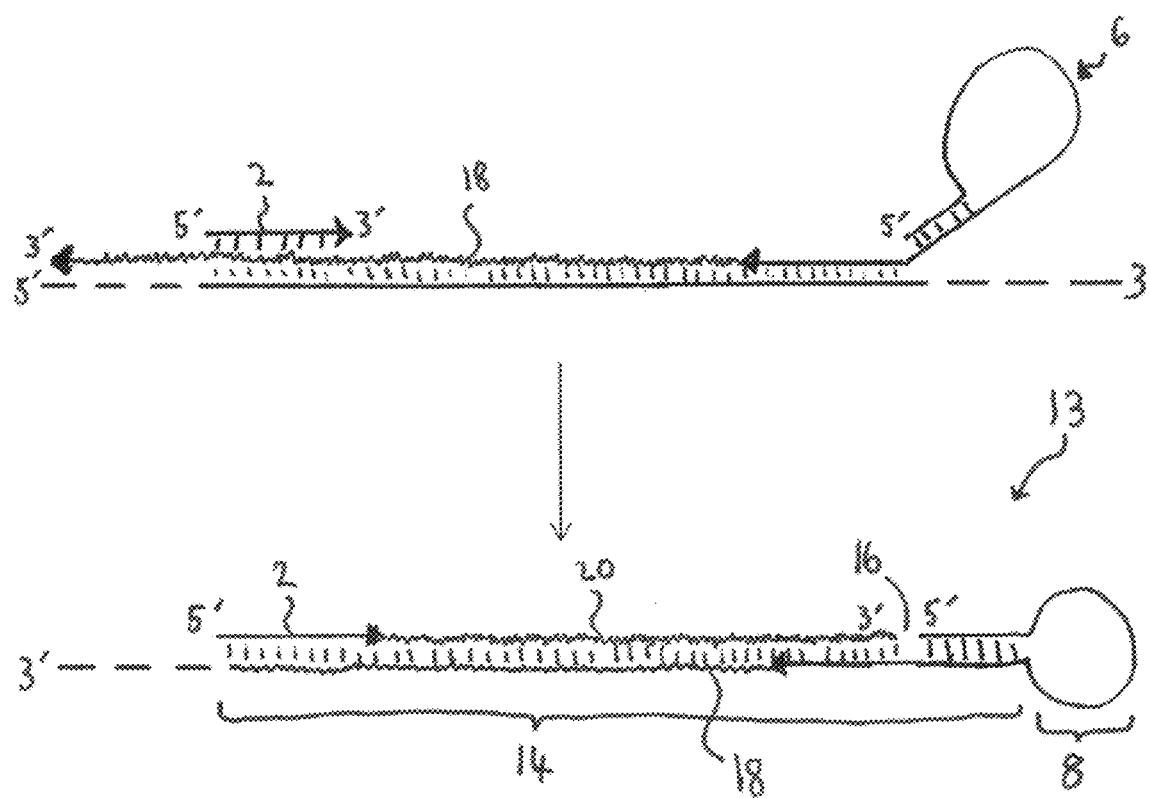
FIG. 2 schematically illustrates some features of the present method.

With reference to FIG. 1, some embodiments of the present method may comprise (a) producing a reaction mix comprising: a nucleic acid sample, a polymerase, nucleotides, a forward primer 2 that hybridizes to a sequence in the bottom strand of fragment 4 in the sample and a reverse primer 6, wherein the reverse primer has a hairpin structure comprising a loop 8, a stem 10 and a 3' overhang 12 of at least 8 nucleotides, wherein the 3' overhang hybridizes to a sequence in the top strand of the fragment 4, and (b) subjecting the reaction mix to at least two rounds of denaturation, renaturation and primer extension conditions (which may be done by, e.g., altering the reaction mix or by thermocycling) to extend the forward and reverse primers to produce an amplification product. As shown in FIG. 2, amplification product 13 contains: i. a double stranded region 14 comprising a nick 16 that is adjacent to the 5' end of the reverse primer, and ii. the loop 8 of the first hairpin primer. An example of the primer extension reactions that can produce amplification product 13 are shown in FIG. 2. In some cases, after the first round of denaturation, renaturation, and primer extension, reverse primer 6 is extended to produce primer extension product 18. After a subsequent round of denaturation, renaturation, and primer extension, forward primer 2 is extended to produce primer extension product 20. In amplification product 13, primer extension products 18 and 20 are complementary. In some embodiments, the primer extension reactions is done using a polymerase under non-strand-displacing conditions (e.g., by using a polymerase lacking this activity) so that stem 10 remains as a duplex. Further rounds of denaturation, renaturation, and primer extension will produce more of the same product.

In some embodiments, the method may comprise sealing the nick 16 with a ligase. In these embodiments, the 5' end of reverse primer 6 should be phosphorylated (either during oligonucleotide synthesis, or enzymatically) to enable efficient sealing of the nick. After the nick is sealed, the method may comprise subjecting the reaction mix to at least two rounds of denaturation, renaturation and primer extension conditions (e.g., at least 2, at least 4, at least 8, at least 10, at least 15 or at least 20 cycles) to amplify a concatemerized amplification product. As will be discussed in greater detail below, this embodiment of the method may be done using a forward primer which, itself, is a hairpin primer.

The part of the primers that hybridizes to the fragment (which may be at least 8, at least 10 or at least 12 nucleotides in length) may be locus-specific (i.e., they hybridize to specific sites in opposite strands that are separated by, e.g., 100 bp to 10 kb), or they may contain some level of degeneracy. In some embodiments, the primers may have a random sequence at their 3' ends. In some embodiments, and as will be explained in greater detail below, the primers may hybridize to adaptor sequences that have been added to a library of fragments, e.g., a sequencing library. In these embodiments, the method may be used to non-specifically amplify a nucleic acid library before analysis, e.g., before sequencing. In some embodiments, the part of the primers that hybridizes to the fragment may hybridize to overhangs created by digestion by an endonuclease.

In some embodiments, forward primer 2 may be a linear primer (i.e., with little or no secondary structure) and may or may not contain a 5' tail. In other embodiments and as will be described in greater detail below, forward primer 2 may be a hairpin primer. In some embodiments (and as discussed in greater detail below), the forward primer may have a hairpin structure comprising a loop, a stem and a 3' overhang of at least 8 nucleotides, wherein the 3' overhang hybridizes to a sequence in the bottom strand of the fragment, and wherein the amplification product further comprises the loop of the forward primer at the opposite end to loop of the reverse primer. In these embodiments, further amplification cycles will produce a concatemerized product.

In some embodiments, the 5' end of the forward primer is not a 5' phosphate and, as such, may have an unligatable 5' end. In some embodiments, the 5' end of the reverse primer is a 5' phosphate, thereby allowing the end of the primer to be ligated the hydroxylated 3' end of a primer extension product. In some embodiments, both primers may be free in solution. In some embodiments, the forward primer may be tethered to a support, e.g., by its 5' end. Use of a forward primer that is tethered to a support should result in an amplification product that is tethered to the surface of the support.

In some embodiments, a plurality of the strands of fragments in the sample are asymmetrically tagged with a 5' adaptor sequence and a 3' adaptor sequence, and the 3' overhang of the forward primer hybridizes to the 3' adaptor sequence and the 3' overhang of the reverse primer hybridizes to the complement of the 5' adaptor sequence. In these embodiments, fragments may be "asymmetrically tagged" in the sense that on any one strand the 5' end adaptor sequence is not the same as or complementary to the 3' adaptor sequence. Further, either or both adaptors may contain a sample index or a molecular barcode, or both, and the primers may prime upstream of the index and or barcode sequences, thereby allowing the index and or barcode to be copied. A population of asymmetrically tagged fragments may be extracting DNA from a biological sample, fragmenting it (if it is not already fragmented) and adding adaptor sequences to the ends. In these embodiments, the initial steps may be mediated by a transposase (see, e.g., Caruccio, Methods Mol. Biol. 2011; 733:241-55), in which case the fragmentation and tagging steps may be done simultaneously, i.e., in the same reaction using a process that is often referred to as "tagmentation". In other embodiments, the fragmenting may be done mechanically (e.g., by sonication, nebulization, or shearing) or using a double stranded DNA "dsDNA" fragmentase enzyme (New England Biolabs, Ipswich Mass.). In some of these methods (e.g., the mechanical and fragmentase methods), after the DNA is fragmented, the ends may be polished and A-tailed prior to ligation to the adaptor. Alternatively, the ends may be polished and ligated to adaptors in a blunt-end ligation reaction. In other embodiments, the DNA in the initial sample may already be fragmented (e.g., as is the case for FPET samples and cell-free DNA (cfDNA), e.g., ctDNA, samples). In some cases, the fragments in the sequence library may have a median size that is below 1 kb (e.g., in the range of 50 bp to 500 bp, or 80 bp to 400 bp), although fragments having a median size outside of this range may be used.

In some embodiments, a population of asymmetrically tagged fragments may be made by ligating the DNA to a universal adaptor, i.e., an adaptor that ligates to both ends of the fragments of DNA in the sample. In certain cases, the universal adaptor may be added by ligating a Y adaptor (or hairpin adaptor) onto the ends of the DNA in the sample, thereby producing a double stranded DNA molecule that has a top strand that contains a 5' tag sequence that is not the same as or complementary to the tag sequence added the 3' end of the strand. In some embodiments, this step may require polishing (i.e., blunting) the ends of the DNA with a polymerase, A-tailing the fragments using, e.g., Taq polymerase, and ligating a T-tailed Y or hairpin adaptor to the A-tailed fragments. In these embodiments, a "Y-adaptor" refers to an adaptor that contains: a double-stranded region and a single-stranded region in which the opposing sequences are not complementary. The end of the double-stranded region can be joined to double stranded fragments such as double-stranded fragments of genomic DNA, e.g., by ligation. Each strand of an adaptor-tagged double-stranded DNA that has been ligated to a Y adaptor is asymmetrically tagged in that it has the sequence of one "arm" of the Y-adaptor at one end and the other "arm" of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence. A "hairpin" adaptor is similar to a Y adaptor except the arms are joined by a cleavable linkage and a similar product can be produced by ligating on a hairpin adaptor and cleaving the cleaving the cleavable linkage.

In some embodiments, the polymerase used in this method is not strand-displacing, i.e., not a polymerase that is able to displace one or more nucleotides, such as at least 10 or 100 or more nucleotides that are downstream from the enzyme. In some embodiments, the non-strand displacing polymerase is stable and active at a temperature of at least 50° C. or at least 55° C. In some embodiments, the amino acid sequence of the polymerase may be at least 90% identical to (e.g., at least 95% identical to, at least 98% identical to or at least 99% identical to) the amino acid sequence of a naturally occurring bacterial or archaebacterial polymerase such as a polymerase from *Pyrococcus* or *Thermococcus*. Exemplary archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase (New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9o N-7 DNA polymerase; *Thermococcus* sp. NA; *Pyrodictium occultum* DNA polymerase; Methanococcus voltae DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2; etc.

The length of any overhang may be at least 8, at least 10, or at least 15 nucleotides. The length of any loop may be at least 4, at least 6, at least 8 or at least 10 nucleotides. Finally, the length of any stem may be less than 30, less than 20 or less than 15 nucleotides. In many embodiments, the duplex in a stem may have a relatively high Tm, e.g., a Tm of at least 70° C., at least 80° C. at least 90° C. at least 95° C., or a Tm that is at least 10, 15 or 20° C. higher than the Tm of the loop sequence, thereby facilitating intramolecular priming events (rather than intermolecular priming events). In some embodiments, the sequence of the loop may by A/T rich (e.g., composed of at least 60%, at least 70% or at least 80% As and/or Ts) and may have a relatively low Tm (e.g., a Tm of below 60° C., below 50° C., or below 40° C.).

Examples of how to implement the method described above are set forth in greater detail below. In the implementations shown in FIGS. 3-5 and FIG. 9 and FIG. 11, both primers are hairpin primers. In the implementations shown in FIGS. 6-8 and FIG. 10, the forward primer is linear primer, i.e., not a hairpin primer.

Figure 3:
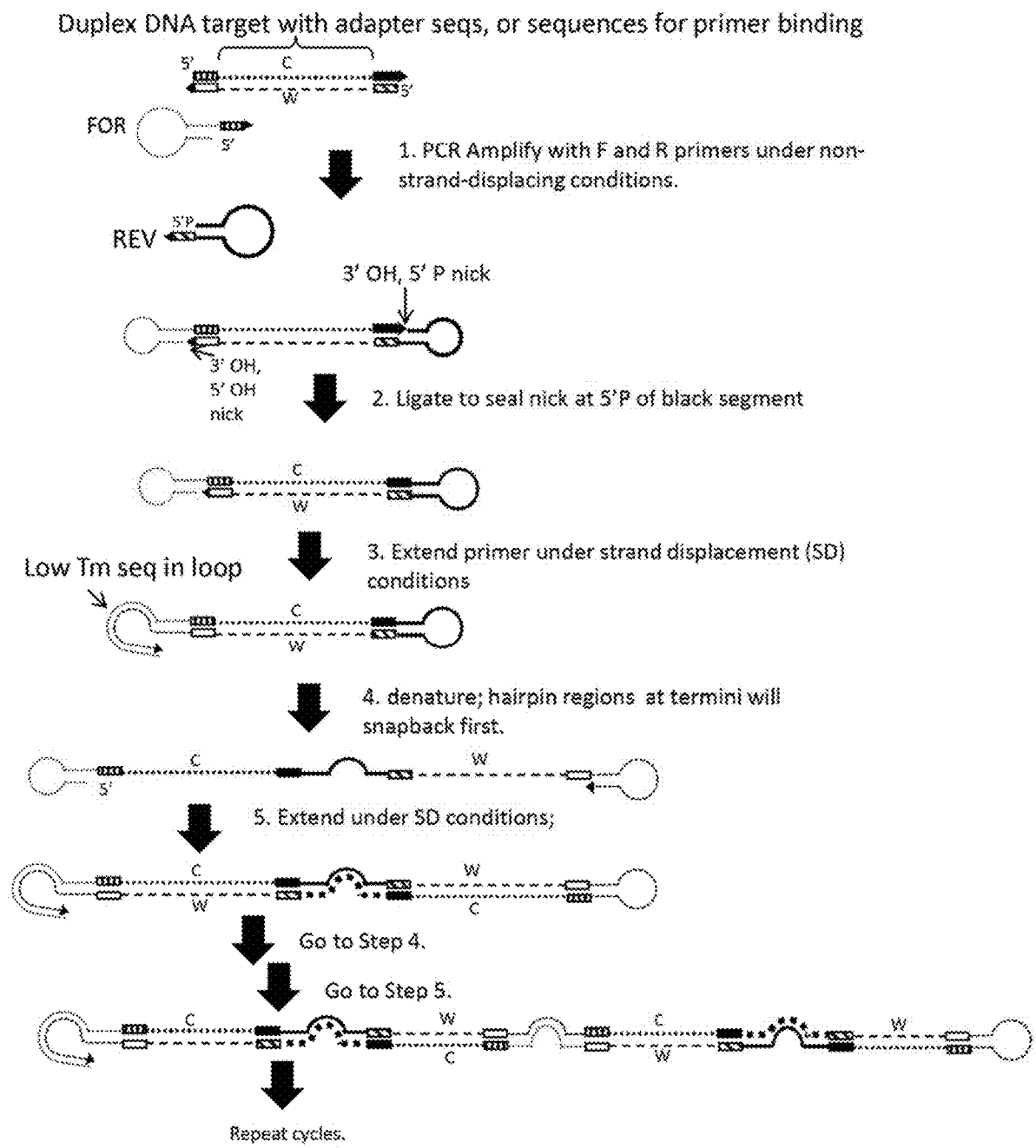
FIG. 3 schematically illustrates a double hairpin implementation of the method. Each cycle doubles length of product as well as the number of copies of w and c strands. Ladder of products may form as internal sites are primed by hairpin products.
Figure 4:
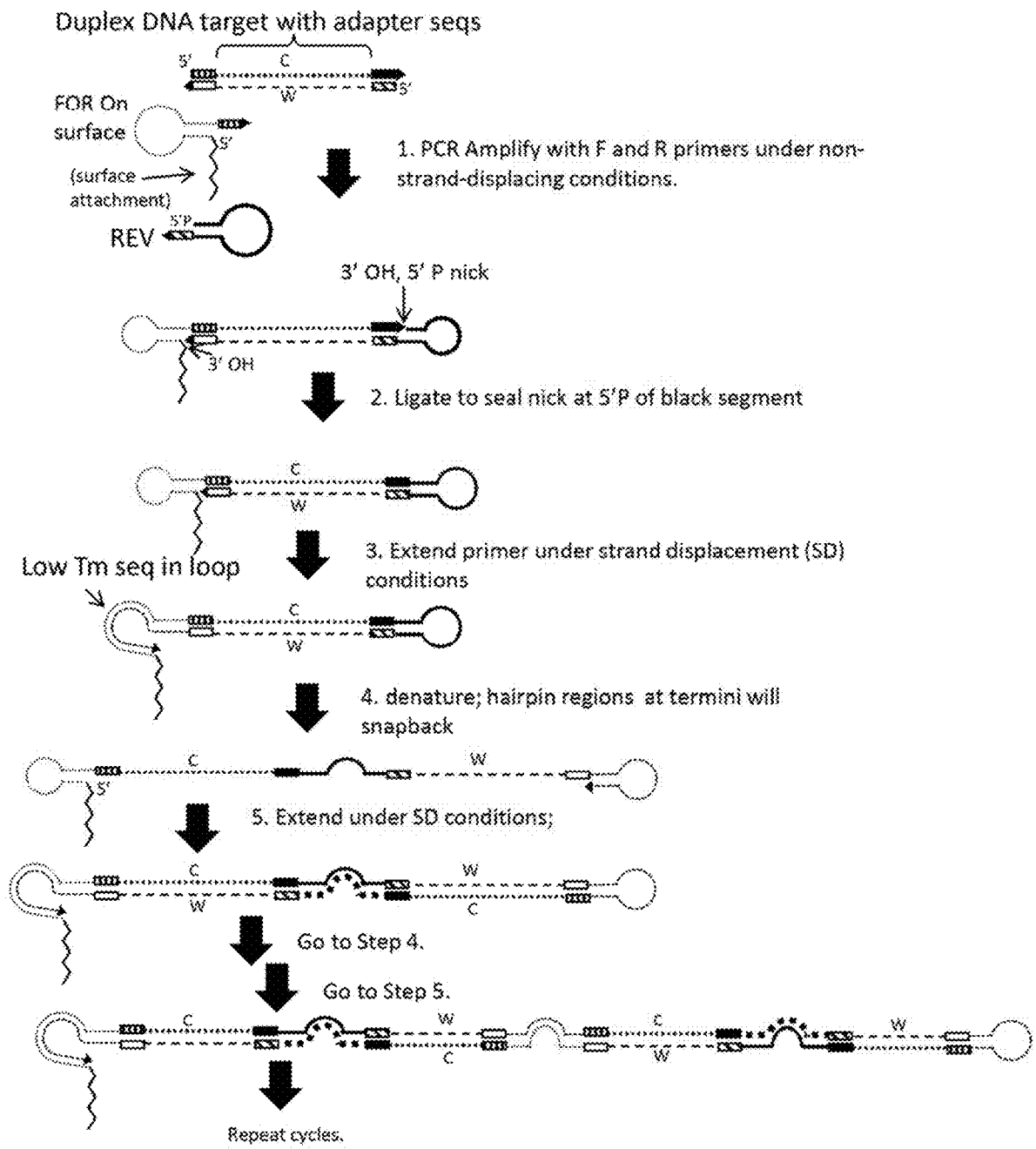
FIG. 4 schematically illustrates a method for amplifying a double hairpin molecule on a surface. Each cycle doubles length of product as well as the number of copies of w and c strands. Ladder of products may form as internal sites are primed by hairpin products.

FIG. 3 describes a solution phase amplification method which does not require addition of primers after the first step. In the first step, two hairpin primers are added, using non-strand-displacing (SD) conditions, creating a dumbbell structure. In some embodiments, the dumbbell amplification products may be purified after this step, removing unused primers, polymerase, and/or nucleotides. The reverse primer should have a 5' phosphate, allowing ligation in step 2. In step 3, a strand-displacing polymerase will extend the forward primer to the end of the dumbbell. In step 4, the dumbbell is denatured, but the sequences of the stem-loop reverse and reverse primers is designed such that denaturation/annealing or hybridization conditions can be chosen to allow rapid re-annealing of the stem regions (relative to reformation of the hairpin structure shown after step 3), creating a substrate with two hairpin ends. For example, the loop region may be designed at AT-rich, and the stem region may be designed with a relatively higher GC content. For example, an oligonucleotide may be included which binds to part of all of the REV primer, creating a duplex region that may disfavor formation of the stem in the REV primer, and creating a more rigid region in the molecule represented after step 4 of FIG. 3. Alternatively, the loop structure of the FOR primer could contain sequences which encourage stable, efficient hairpin formation as described in Varani (Annu. Rev. Biophys. Biomol. Struct. 1995 24: 379-404). When the 3' OH is extended by a strand-displacing polymerase in Step 5, it creates a structure similar to the structure in Step 3, except that the insert region has been duplicated. Double arrows at the bottom of the FIG. 4 represent how steps 4 and 5 can be repeated, resulting in a doubling of the length of the product, and a duplication of the insert region (dotted lines labeled w and c). As the length of the concatemer increases, the likelihood of the 3' end folding back to form the hairpin loop, or the likelihood of the 3' end of the duplex binding to an internal priming site, will increase relative to the likelihood of the entire duplex reannealing, as the increasing length will decrease the local concentration of the 5' and 3' ends relative to one another. As long as the 3' end of the concatemer hybridizes to an internal site, and not to the 5' end, extension of the 3' end by a polymerase will amplify at least part of the sequence.

If the 3' end binds to an internal priming site, a 5' flap structure may be formed. In some embodiments, this flap structure may be cleaved by a flap endonuclease or FEN activity, which will reduce the length of the concatemer and generate DNA fragments of the sequence in the flap.

In some embodiments, some of the concatemers may be captured by a target enrichment process. For example, one or more concatemers in a mixture may be targeted by Cas9 protein, as described in US 2014/0356867. For example, the w or c sequences may be targeted by one or more hybrid selection probes such as those used in the SureSelect technology commercialized by Agilent Technologies. The fraction of amplification products captured by the target enrichment process may be 50%, 200/o, 10%, 5%, 1%, 0.01% or less of the total sequences in the mixture. An important feature many embodiments of the present method is that the amplified DNA is created as a concatemeric sequence, wherein the copies are all connected. This feature may be exploited together with other methods, such as deep sequencing, target enrichment, PNA-mediated PCR clamping, or molecular barcoding, to enable analysis of rare alleles. For example, if a mutation is present in a sample at an allele frequency below 0.5%, the intrinsic error rates of many analysis methods (such as next-generation sequencing) can make the mutation difficult to detect with high accuracy. Using the present method, many tandem copies of the rare allele can be created in the same molecule. When the amplification product containing the rare allele is analyzed (possibly after target enrichment), the tandem copies should enable measurement of the rare allele with high accuracy. In some embodiments, the amplification products containing the rare allele may be enriched relative to products not containing the rare allele (e.g., containing the wild type sequence). For example, amplification products containing the wild type sequence may be digested by a restriction enzyme, or by a Cas9 nuclease, or by a TALEN protein. For example, the hairpin amplification method, or a subsequent PCR amplification, may be done in the presence of a PNA complementary to the wild type sequence, as in PNA-mediated PCR clamping. For example, amplification products containing the rare allele may be enriched by allele-specific PCR, or by target enrichment methods for DNA sequencing.

Figure 9:
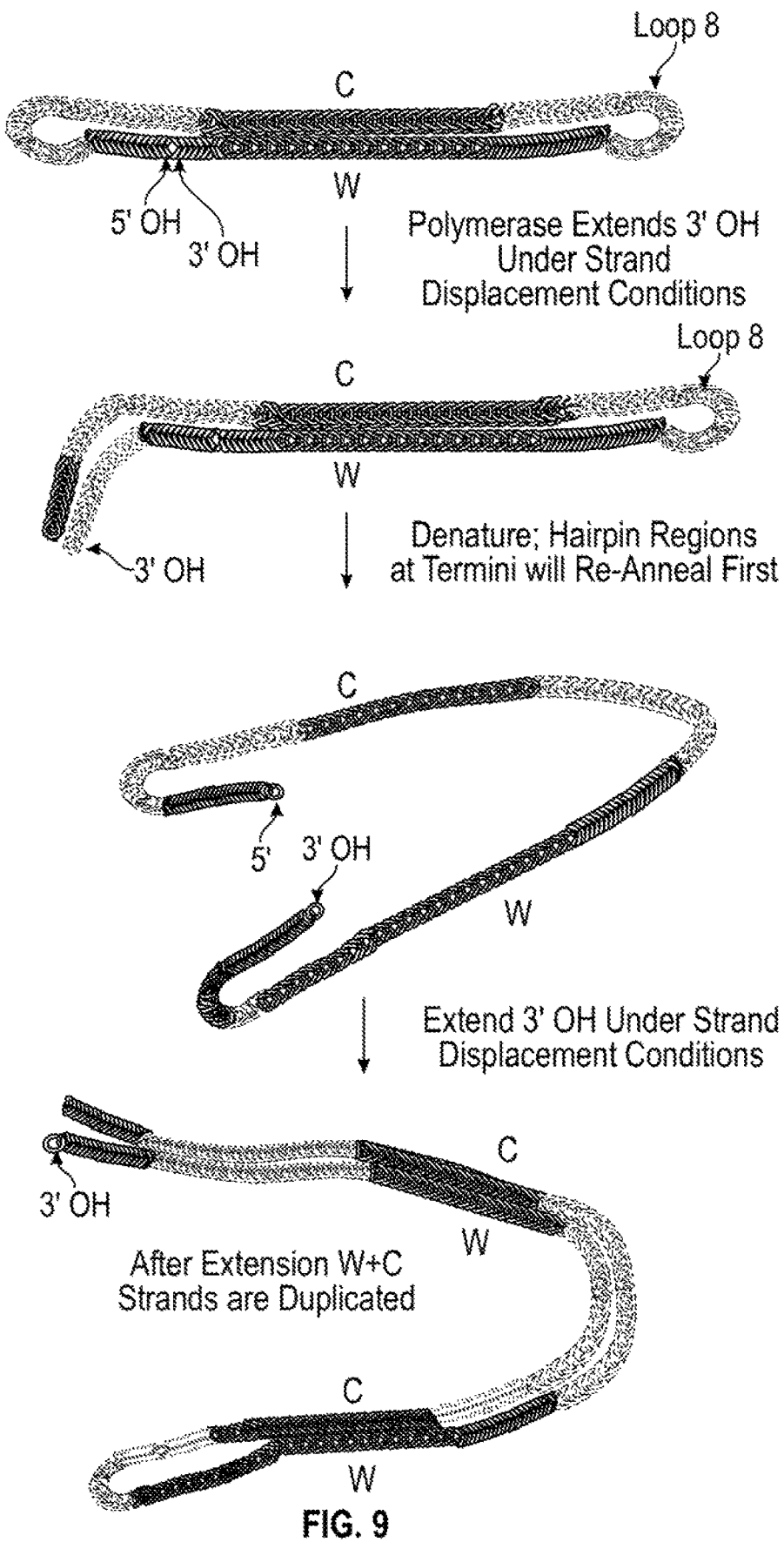
FIG. 9 schematically illustrates a double hairpin implementation of the method, using a physical model to illustrate certain features of the method.

To further clarify the denaturation, annealing, and duplication processes, a physical model representing some of these steps is shown in FIG. 9.

FIG. 4 shows an embodiment of the same method, except the forward primer is surface-attached at the 5' end. Various attachment strategies can be used, such as biotin-streptavidin, or direct covalent coupling to silanized glass, covalent coupling of the primer to a hydrogel on a surface, covalent coupling to a bead, etc.

Figure 5:
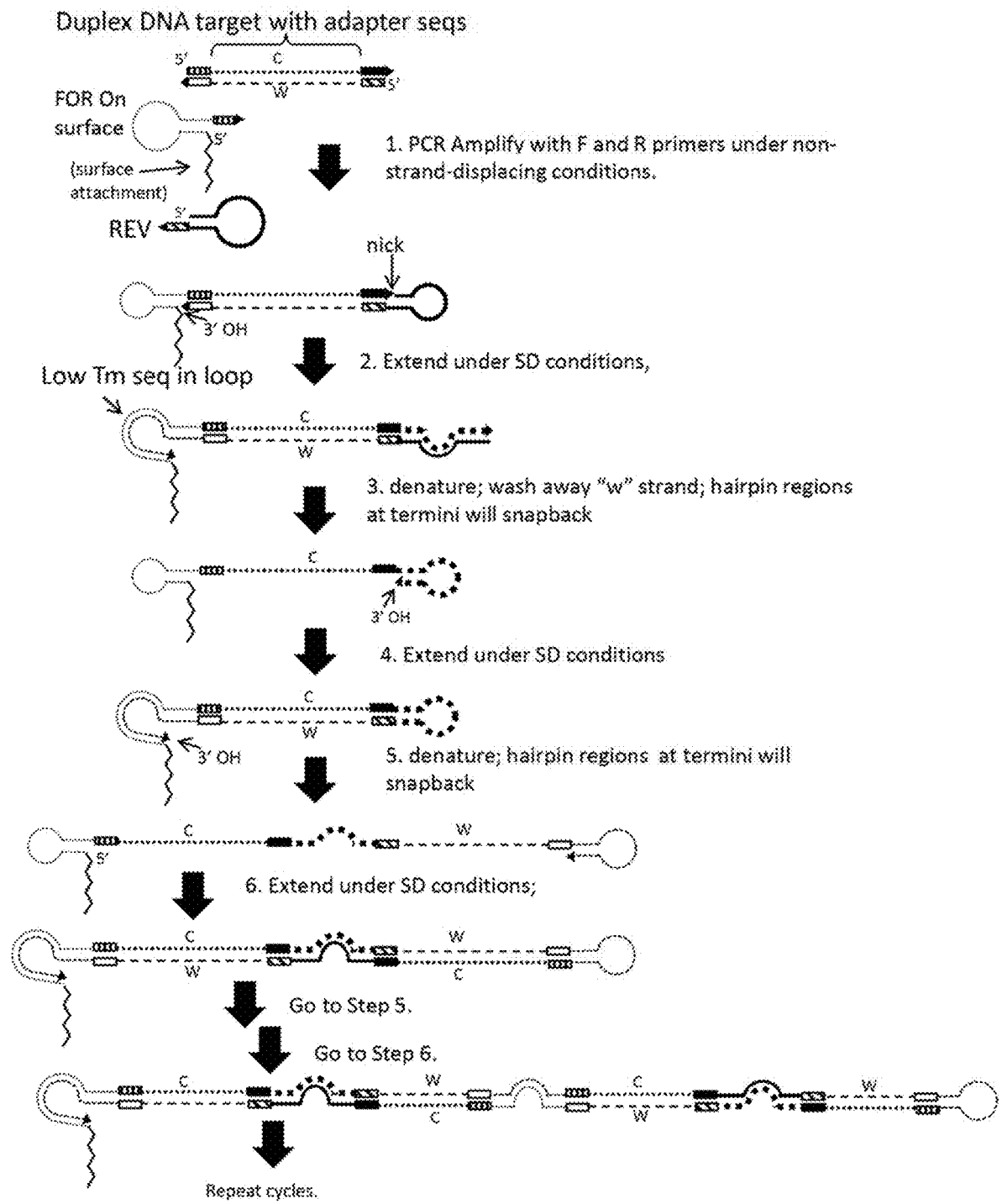
FIG. 5 schematically illustrates an implementation that uses a strand-displacing polymerase in the first step. Each cycle doubles length of product as well as the number of copies of w and c strands. Ladder of products may form as internal sites are primed by hairpin products.

FIG. 5 shows an embodiment using a strand displacing polymerase in the first step. In this embodiment, no ligation step is necessary. The main result is that only a single strand (e.g., Crick) of the original insert is retained, and the other strand may be washed away or captured by other features of the surface, which may comprise sequences designed to hybridize to the w strand (not shown). However, the later cycles of amplification are similar to FIG. 4, or could easily be adapted to solution phase as in FIG. 3 or FIG. 11. In some embodiments the product may grow in length enough to contact other surface bound primers. During the denature/ anneal step, these surface bound primers may also bind and prime synthesis of the dumbbell, creating more copies and more surface attachment sites.

Moreover, if one primes from a site in an internal loop using a 3' up primer on a solid surface, a mixture of product lengths will be created. A cluster of molecules can still be created from a single template molecule, but the mixture of lengths may mitigate the risk that a single break would remove the clone from the surface (i.e., each internal loop-priming event will create another molecule with its own surface attachment). In some embodiments, a hairpin amplification product created in solution may be later amplified on a solid surface. For example, a hairpin amplification product may be combined with a surface containing a pair of 3' up primers (for bridge amplification) or a single 3' up primer for creation of a DNA cluster on the surface, enabling analysis by sequencing. In the case of the single primer on the surface, the structure of the hairpin amplification product may enable DNA cluster generation without addition of a second primer. Similarly, if one amplifies in solution with a mix of hairpin and non-hairpin primers, a mixture of products will be created. All hairpin primers will create a few, very long molecules composed of tandem duplications. Non-hairpin primers will create many short molecules, or a ladder of shorter to longer fragments, as in regular PCR from a concatemeric template. By carefully titrating the ratios of hairpin and non-hairpin primers, the skilled artisan may tune the lengths and numbers of the mixture of molecules. In some embodiments, the hairpin amplification method may be combined with, or followed by another amplification method, such as PCR, SDA, bridge amplification, or wildfire amplification. In some embodiments, the hairpin amplification method may be combined with, or followed by, a selective amplification method, such as PNA-mediated PCR clamping or allele specific PCR, to enrich for rare alleles. Finally, one can encourage melting of the primer-containing loop using a high concentration of "blocker" oligonucleotides that is identical to the reverse primer loop segment shown in FIG. 3, with a terminator to block extension. In some embodiments, the blocker oligonucleotide may form a duplex comprising part of the stem sequence, creating a more rigid region in the middle of the molecule. These "blocker" oligonucleotides can be used to anneal to the internal hairpin and loop segments, or to push the balance towards unfolding of the dumbbell during the denaturation step.

Figure 6:
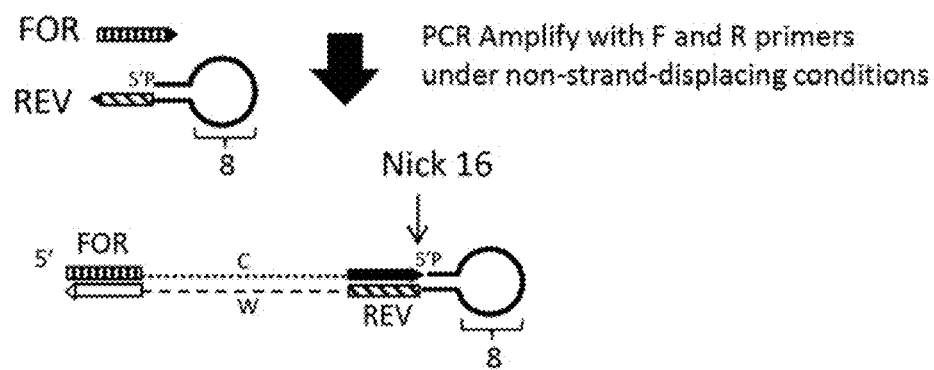
FIG. 6 schematically illustrates a way to amplify a library. Loop 8 is marked to show corresponding part in FIG. 1.

A further implementation is shown in FIG. 6. In the method of FIG. 6, the method starts with a library of unknown target sequences of DNA with adapter sequences on both ends; this is similar to current next generation sequencing libraries for other sequencing platforms. Such libraries may be made by tagmentation, or by ligating a Y- or hairpin adaptor, as discussed above. The two unknown strands are denoted "w" and "c" for Watson and Crick strands (or "top" and "bottom" strands), 3' ends are shown as arrowheads, and the adapter sequences are shown in different shadings. It is important for the unknown target sequence to have different adapter sequences on the 5' and 3' ends, i.e., are "asymmetrically tagged"; for example, the "w" strand may be flanked by FOR on the 5' end and "VER", the reverse complement to REV, on the 3' end, while the "c" strand may be flanked by REV on the 5' and "ROF," the reverse complement to FOR on the 3' end. To prepare the library for surface amplification, the library should be amplified using a reverse primer that contains a hairpin-loop sequence, such that the 5' phosphorylated end folds back and hybridizes to form a duplex (see FIG. 6.) PCR should be performed with a polymerase lacking strand displacement activity (e.g., Taq polymerase.) After this step, which may comprise many cycles of PCR, or as few as two cycles of PCR, the library will comprise molecules as schematically illustrated at the bottom of FIG. 6, duplex molecules with a hairpin loop at one end, and a ligatable nick 16 in the stem region.

In another implementation, adapter sequences are not used, and instead the FOR and REV primers are designed to hybridize to specific sequences in a target sequence, as is known in the art for PCR of a specific sequence. In this implementation, the boxes labeled FOR, ROF, REV, and VER in FIG. 6 may simply be sequences adjacent to the target sequence. For example, the target sequence may comprise a specific fragment of DNA created by restriction digestion, and the FOR and REV sequences may represent sequences found at the end of the restriction fragment. In these embodiments, a target nucleic acid of substantially known sequence (such as a human genomic sample) may be digested with one, two, or more restriction enzymes, creating a set of fragments with known ends. Hairpin primers may be designed to hybridize to the ends of the fragments, creating substrates for amplification by the methods described here (See FIG. 6 and FIG. 11).

Figure 7:
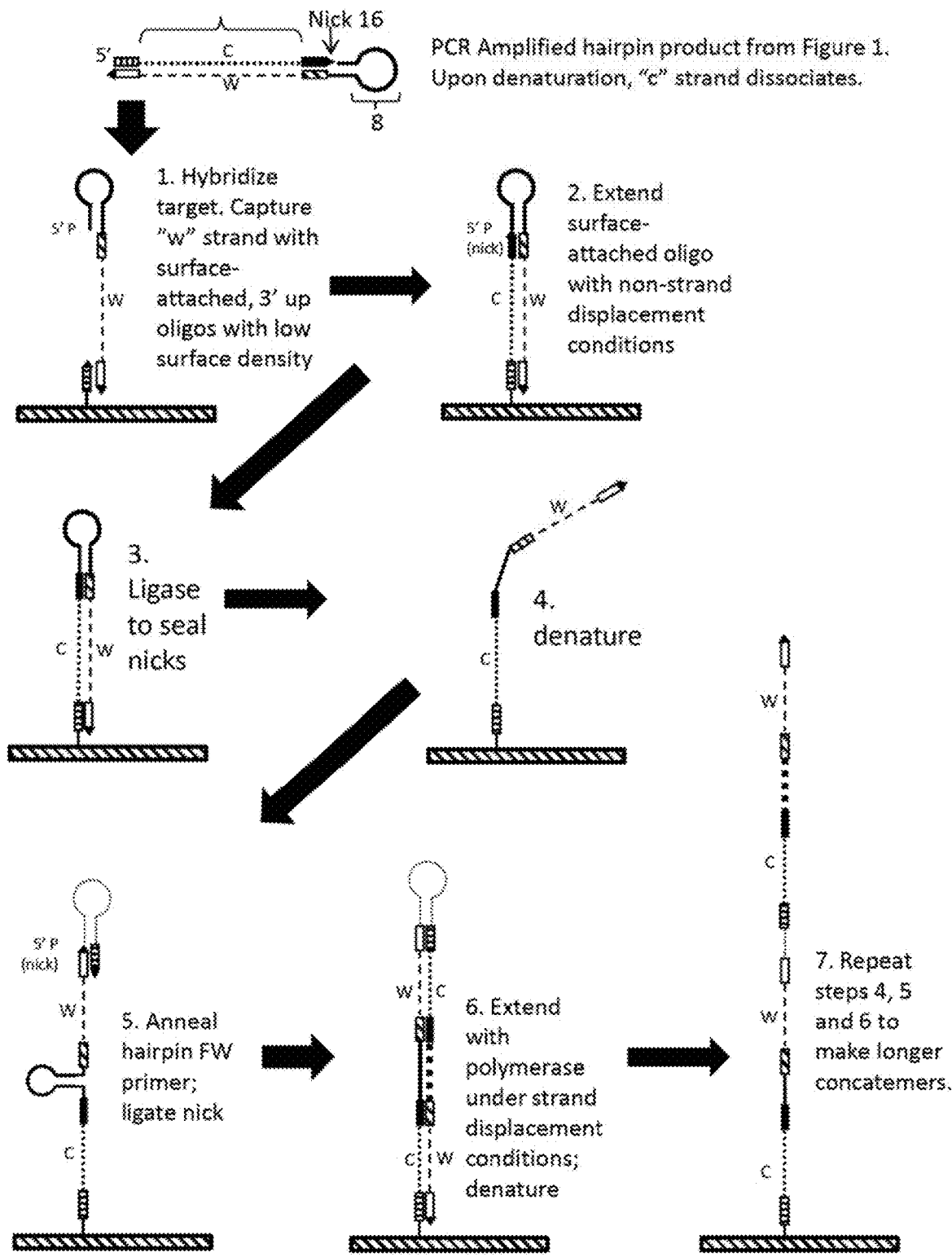
FIG. 7 schematically illustrates a way to generate clusters on a solid substrate.
Figure 8:
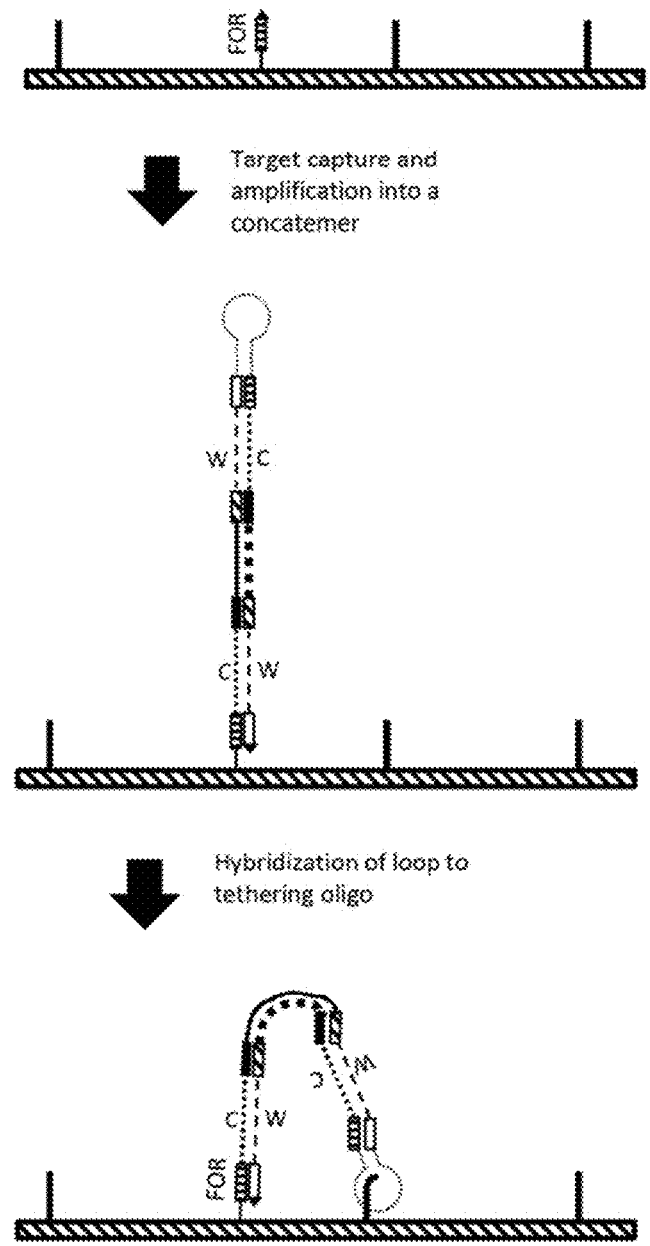
FIG. 8 schematically illustrates the use of a tethering oligonucleotide.

A surface amplification procedure is schematically illustrated in FIG. 7. The surface amplification requires a surface with DNA oligonucleotides bound which have a "3' up" orientation, e.g., primers which are attached to a surface or matrix via their 5' end. These primers could all have a common sequence, i.e., the surface could be coated with many individual copies of the same oligonucleotide, and this primer should comprise the "FOR" sequence illustrated in FIG. 7. In some embodiments described in more detail later, the surface may also be coated with a second, third, fourth, or more sequences, which may be interspersed with the FOR oligonucleotides.

In the first step of this method (FIG. 7, "1. Hybridize target"), a dilute solution of target molecules is hybridized to the 3' up oligonucleotides on the surface. The target molecules may comprise a library of many different sequences, but each molecule in the library should have common adapter sequences on the 5' and 3' end. The common sequences may be attached by ligation, for example. In step 1, the sequence on the 3' end of the target (white box) hybridizes to the surface-bound oligonucleotide. The 5' end of the target comprises a common sequence (black solid line) which folds back on itself to form a hairpin-loop structure, and furthermore, the 5' terminus should be phosphorylated. The unknown target sequence (denoted "w" for Watson strand) connects the adapter sequences; the library may comprise many different unknown target sequences which may be amplified by this method in parallel, but a single example is shown for clarity. At the end of step 1, the surface bound oligonucleotide (horizontal striped box) comprises a primer which is hybridized to the target/template.

In the second step, a DNA polymerase which lacks strand-displacement (SD) activity extends the 3' end of the surface-bound primer. This extension will copy the "w" strand, creating the complementary strand denoted "c" for Crick, and thus creating a total of 2 copies of the target sequence. For the purposes of this description, we denote each strand as a copy, rather than each duplex; the extended duplex contains two complementary copies, denoted "w" and "c". The polymerase should proceed only to the 5' end of the target, leaving a 3'-OH, 5'-P nick which can be sealed by DNA ligase activity. At the end of step 2, there is a long duplex DNA, with the 5' end surface-bound, and hybridized to the 3' end, while a hairpin loop structure exists at the surface-distal end.

In step 3, a DNA ligase activity (e.g., T4 DNA ligase enzyme) is added to seal nicks, which will result in covalent attachment of the target strand to the surface.

In step 4, this duplex is denatured by chemical, enzymatic or physical means, creating an extended target. For example, NaOH, or helicase activity, or heating above the melting temperature may be sufficient to denature the duplex. In some embodiments, the hairpin structure (black solid line) may remain paired while the rest of the duplex is substantially denatured.

In step 5, a primer with a hairpin structure and 5' phosphate (thin dotted line) is hybridized to the 3' end of the extended target. This annealed primer may have an identical 3' sequence to the surface-bound primer (horizontal striped box), but the 5' end comprises a hairpin-loop structure, such that upon annealing to the 3' end of the extended target (white box), a ligatable nick is created. The thin dotted linehairpin primer may need to be added a high concentration to displace the surface-proximal sequence (horizontal striped box). Also, the "w" and "c" strands are likely to re-anneal during this step but are shown in the extended conformation for clarity. DNA ligase activity seals the nick between the 5' end of the thin dotted line hairpin primer and the 3'OH, leaving a primer-template complex with free 3' OH.

In step 6, DNA polymerase activity with strand displacement activity extends the 3' OH back towards the surface. This extension by a SD-polymerase should denature and copy the hairpin segment in the middle of the duplex (shown as a black solid line), creating a reverse complement sequence (thick dashed line) which will also be capable of folding into a hairpin. This extension makes a second copy of both the w and c segments and resulting in 4 total copies of the target segment. At the end of step 6, there is a long hairpin duplex DNA which is covalently attached to the surface, approximately twice the length of the hairpin duplex from step 2.

In step 7, the hairpin duplex is denatured and the target DNA is shown in extended conformation, similar to step 4. Steps 4, 5, and 6 can be repeated to make longer concatemers. In summary, repetition of these steps anneals and ligates a hairpin primer to the distal end of a surface-bound target DNA, extends that primer, and thus doubles the length of the surface-bound target DNA. Each cycle also doubles the number of copies of "w" and "c" segments, resulting in exponential amplification of the target sequence on the surface.

Although this method could create many copies of the target sequence, the copies exist as a single concatemer of DNA with a single attachment to the surface. In order to increase stability of the target concatemer, it may be advantageous to include "tethering oligonucleotides" on the surface that could hybridize to the hairpin sequences introduced into the concatemer (See FIG. 8). These oligonucleotides could hybridize to their complement sequence and form an extra point of surface attachment during washing and extension steps. The tethering oligonucleotides could be attached to the surface in a 5' up orientation, or they could comprise 3' up oligonucleotides with a nonextendable 3' end (e.g., 2' 3' dideoxy) so that they would not serve as extendable primers. In some embodiments, there may be several types of tethering oligonucleotides on one surface, and the different types of tethering oligonucleotides may be complementary to different regions of the concatemer or target sequence. In these embodiments, the tethering oligonucleotides may also serve to inhibit complete reannealing of the concatemer. In some embodiments it may be advantageous to have a higher concentration of the tethering oligonucleotides than the 3' up FOR oligonucleotides, as each target concatemer would start from a single FOR primer but may eventually contain many copies of a sequence complementary to the tethering oligo. In these embodiments, the relative concentrations of the surface oligonucleotides may be adjusted to allow a certain surface density of clusters. Alternatively, the surface oligonucleotides, particularly the FOR oligonucleotides, may be arranged in an ordered fashion, enabling the amplification of clusters in an ordered array. There may be many other possible variations of this surface amplification method.

Figure 10:
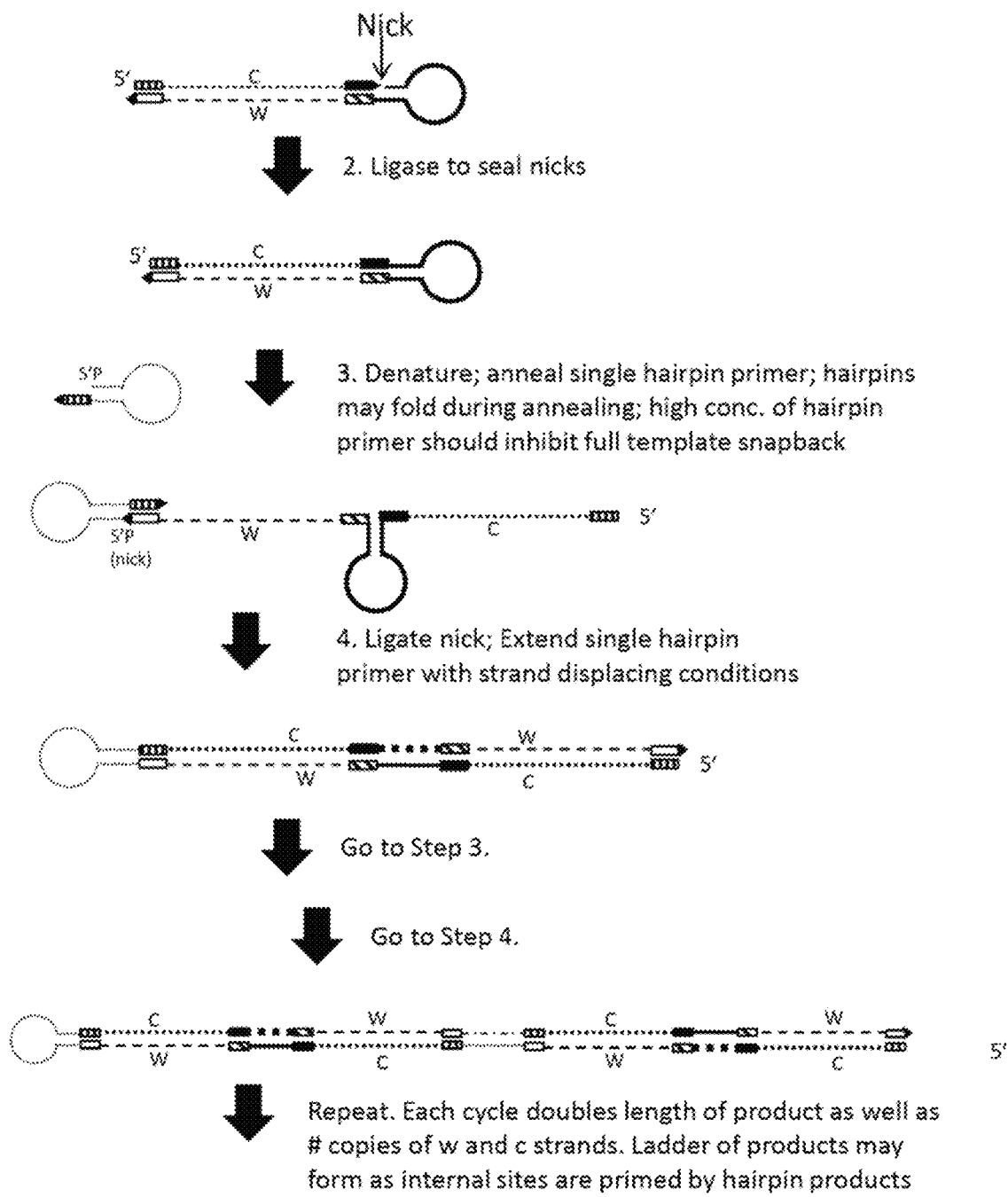
FIG. 10 schematically illustrates a method for amplifying DNA in solution, involving ligation of a hairpin primer.

FIG. 10 shows an embodiment of the invention which is similar to FIG. 7, except that the amplification occurs in solution. In contrast to amplification methods such as PCR, the amplification products are maintained as a single concatemeric molecule, containing many tandem copies of the target sequence. This feature may be particularly advantageous for single-molecule analysis methods such as optical mapping, single molecule real-time (SMRT) sequencing as described by Pacific Biosciences corporation, DNA combing, or nanopore sequencing. Though many single molecule methods have high error rates, the tandem copies may be used to create a consensus sequence representing the original sequence. Furthermore, both the w and c sequences may be analyzed in series as they exist on the same strand of the concatemer. In some embodiments, one or both strands of the concatemer is analyzed by passage through a nanopore. In some embodiments, the concatemer is treated with endo- and or exonucleases prior to analysis, creating a nicked or gapped duplex. In embodiments, labeled or unlabeled primers or other oligonucleotides may be annealed to the nicked or gapped duplex to aid in analysis. For example, concatemers with gaps where parts of the w sequence is removed may be probed with a labeled oligonucleotide complementary to a sequence in certain c strands; in this way, concatemers comprising particular c sequences may be detected or analyzed.

Figure 11:
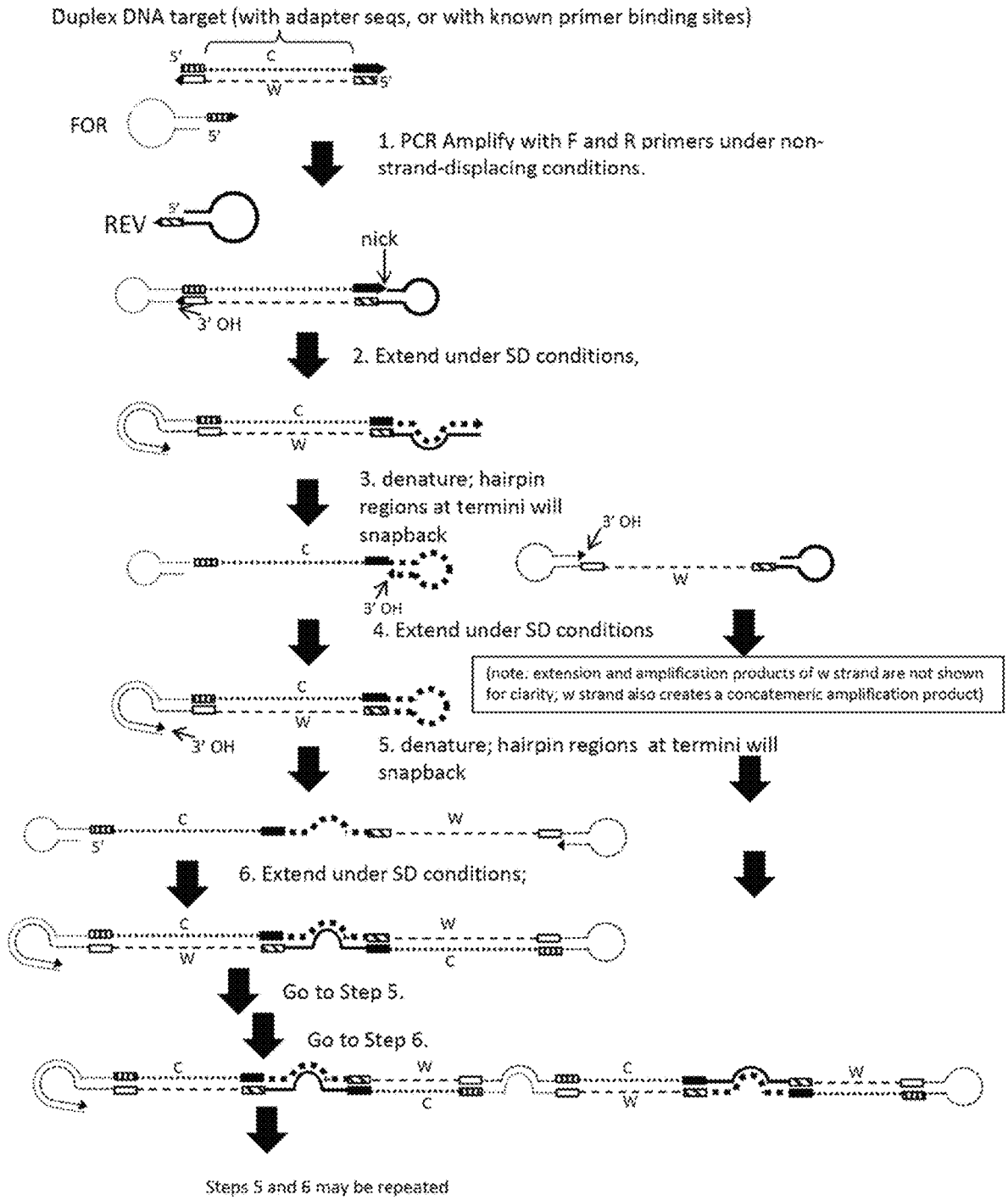
FIG. 11 schematically illustrates a method for amplifying DNA in solution, without ligation. Each cycle doubles length of product as well as # copies of w and c strands. Ladder of products may form as internal sites are primed by hairpin products. Both the w and c strands of the original molecule will create concatemeric amplification products containing multiple copies of the w and c sequences, as well as the hairpin and adapter sequences.

FIG. 11 shows an implementation of the invention illustrating amplification in solution. In this implementation, a target DNA with asymmetric adapters may be used, or a target DNA may be amplified from a larger sequence by designing hairpin primers with 3' extensions complementary to sequences adjacent to the target sequences, using PCR primer design strategies known in the art. In this implementation, neither the FOR nor the REV primer requires a 5' phosphate. After the target sequence is amplified by PCR under non-strand displacing conditions (step 1), a dumbbell product with two nicks is created. The PCR product may be purified after the initial PCR, if desired, removing excess FOR and REV primers. This dumbbell DNA is then subjected to primer extension by a polymerase under strand displacing conditions, creating a duplex molecule (step 2.) This molecule is denatured (step 3), separating the w and c strands, and the hairpin regions at the ends of the w and c molecules will reanneal as described above. Subsequent cycles of polymerase extension (step 4) and denaturation (step 5) will make copies of the w and c sequences, creating a DNA concatemer in a fashion akin to a folding carpenters ruler. FIG. 11 schematically illustrates the steps only for the c strand, but as will be understood by those skilled in the art, application of the steps will also create a similar concatemer from the w strand. Each concatemeric molecule will contain tandem copies of the w and c strands, interspaced by known sequences from the hairpin primers. It will be appreciated by those skilled in the art that this molecule may be a useful substrate for sequencing. For example, a single concatemeric molecule contains many copies of the target sequence, allowing sequence determination of many segments in parallel, thus amplifying the signal. Also, a single primer (potentially even the 3' end of the molecule, after it has snapped back as a hairpin) could be used to sequence both the w and c strands, provided the sequencing read is long enough. Also, it will be evident to the skilled artisan how this molecule may be used for "paired end" sequencing, using one primer which anneals to the region adjacent to the w strand (white box) for one read, and a primer which anneals to the region adjacent to the c strand (black box) for the second read. Also provided are a variety of primer systems that may comprise two or more primers. In certain embodiments, such a system may comprise: (a) a forward primer that hybridizes to a sequence in the bottom strand of a fragment in a sample; and (b) a reverse primer, wherein the reverse primer has a hairpin structure comprising a loop, a stem and a 3' overhang of at least 8 nucleotides, wherein the 3' overhang hybridizes to a sequence in the top strand of the fragment. In some embodiments, the forward primer has a hairpin structure comprising a loop, a stem and a 3' overhang of at least 8 nucleotides, wherein the 3' overhang hybridizes to a sequence in the bottom strand of the fragment. The overhangs of the forward and reverse primers may or may not be complementary to, or the same as, naturally occurring sequences from a cell. In some embodiments, the overhangs are complementary to or identical to all of or a portion of adapter sequences which have been ligated to target DNAs. In some embodiments, the target DNAs comprise sequences which substantially represent the entire genome, or 50%, 10%, 1%, or less, of the genomic sequence of an organism. In certain embodiments, one or both of the overhang sequences are designed to be complementary to the ends of fragments of DNA created by digestion with one or more restriction enzymes. In some embodiments, the overhangs of the forward and reverse primers are designed to be complementary or identical to sequences in a target gene or genomic region. In these embodiments, the primer system may be used to amplify or enrich target sequences prior to analysis by methods known in the art, such as PCR or sequencing. In some embodiments, one primer has a 5' phosphate and the other has an unligatable 5' end. In some embodiments, one of the primer may linked to a solid support by its 5' end. In some embodiments, more than one type of forward or reverse primer may be used. In some embodiments, one or more of the primers may include a cleavable site that can be cleaved by an enzyme, such as a deoxyuracil or one or more ribonucleotides. In some embodiments, one or both of the loop regions may contain a cleavable site. In some embodiments, a cleavable site in a loop region may be cleaved to convert the hairpin into a Y-shaped adapter. In some embodiments, one or more of the primers may include a termination region that inhibits progression of the polymerase, such as an abasic site, or a deoxyuracil. If a mixture of primers with and without termination regions is used, altering the fraction of primers containing termination regions may control the length of the concatemer in the reaction.

In some embodiments, the primers may include recognition sequences for restriction endonucleases or nicking enzymes, which may be used to create single or double stranded breaks in the molecules during or after amplification. These precisely created breaks may be useful for subsequent analysis. For example, a long amplified concatemeric molecule containing many copies of the target sequence may be digested by a restriction enzyme into many short fragments of the same length, facilitating cloning into a vector, length analysis by gel electrophoresis, SNP analysis, or microarray analysis. For example, the primer or adapter region of the concatemer may be designed to contain vicinal nick sites, enabling target enrichment as described in U.S. Pat. No. 8,017,328. For example, the adapter sequence 3' adjacent to the w sequence may contain a site for a nicking endonuclease. Subsequently, the nick may be converted into a ssDNA gap by the activity of an exonuclease, such as T7 Exonuclease, or similar enzymes, which may initiate from a nick. Limited digestion with T7 Exo will digest part of the w strand, leaving a 3' end adjacent to a ssDNA gap comprising a ssDNA comprising part of the c sequence. The concatemer may contain many of these gaps, with the critical feature that the 3' ends will all be at the same position. Therefore, these 3' ends may serve as initiation sites for DNA sequencing. One or more polymerases and nucleotides may be added to the molecule, and the polymerase will add nucleotides to the 3' end of the gap (wherein, the duplex adjacent to the gap serves as a primer.) Alternatively, a gap may be created using E. coli Exonuclease III, in which case the 3' ends of the gaps may not all be at the same place. However, in these embodiments, the 3' ends of the gaps could be blocked (e.g., by addition of a dideoxynucleotide) and an unblocked sequencing primer may be annealed to a target region within the gap. In this way, the concatemer may be converted into a template for DNA sequencing using certain polymerases, comprising a primer comprising a 3' OH, adjacent to a single stranded region for which the sequence may be determined by methods known in the art, such as sequencing-by-synthesis using labeled nucleotides. In embodiments, labeled nucleotides may be used. In embodiments, fluorescent nucleotides may be used. In embodiments, reversible terminator nucleotides may be used. In embodiments, Lightning Terminator nucleotides may be used. In certain embodiments, a mixture of four nucleotides, each with a different label, is used to determine the sequence adjacent to the primer.

In some embodiments, the amplification product is analyzed by sequencing, using a polymerase with strand displacement or nick translation activity. In these embodiments, the polymerase may initiate polymerization (and sequencing) at a nick created by a nicking endonuclease, or a "d-loop" created by strand invasion of a short oligonucleotide into a duplex.

In some embodiments described in detail below, after initial primer extension and ligation steps, a nicked dumbbell structure is formed by the hairpin primers (similar to that shown schematically in FIG. 3, after step 3). In these embodiments, the primer system described may enable amplification of a target sequence with the addition of primers. In these embodiments, denaturation and annealing conditions may be chosen to favor intramolecular annealing of the 3' end to complementary internal sequences, and to disfavor full reannealing of the full hairpin duplex structure (for example, fast cooling conditions may not allow enough time for full reannealing). Extension of the 3' end under strand displacing conditions will result in duplication of part or all of the hairpin, creating a longer concatemer and resulting in amplification of a target dumbbell DNA without addition of primer oligonucleotides. This feature may be advantageous for amplification of DNA in small volumes or confined spaces, such as microdroplets, aqueous droplets in an oil-water emulsion, nanofluidic wells or channels, or microfluidic wells or channels. In certain embodiments, a nicked dumbbell DNA molecule created using the methods of the invention may be amplified without addition of primers, using only a polymerase, nucleotides, and appropriate buffer conditions.

The present method may be used to generate long DNA concatemers (e.g., longer than 500 bp) from short target DNAs (shorter than 500 bp). It is known in the art that certain DNA samples, such as cell free DNA, DNA purified from formalin-fixed paraffin embedded (FFPE) samples, or degraded DNA samples, may contain many DNA fragments shorter than 500 bp, shorter than 300 bp, or shorter than 200 bp. Conversely, certain analysis methods such as fluorescent in situ hybridization, nanofluidic analysis, nanopore sequencing, pulsed field gel electrophoresis, single molecule real time sequencing, and the like, may be best suited for analysis of longer DNA fragments, e.g., 2 kilobases, 5 kilobases, 10 kilobases, or longer. Thus, the present method may enable easier analysis of short DNA samples by these or other methods. For example, the present method may be useful for generation of sequencing libraries for nanopore sequencing from cell free DNA. Other details of the primers in this system may be found above, or in the figures.

In some embodiments, it may be useful to size fractionate (e.g., by binding to beads, or by gel electrophoresis) or digest the target DNA before amplification by the present method. In some embodiments, it may be useful to size select the amplification products after amplification, to select for uniform lengths, or to select for amplification products longer or shorter than a desired cutoff.

The present method may be generally used to create an amplification product that can be analyzed, for example, to identify mutations that may be present in a sample. For example, the amplification products may be analyzed by hybridization of a labeled probe. For example, the amplification products may be analyzed by hybridization of a sequencing primer and subsequent sequencing. For example, the amplification products may be analyzed by hybridization to a microarray. In some embodiments, the method may be used to generate or amplify a sequencing library. In these embodiments, the sequencing library may contain a substantially complete representation of the genomic sequence (for example, if adapters are ligated to the target DNA fragments and amplification primers specific for these adapters are used). Alternatively, the hairpin primers may be designed to amplify only a subset of the genomic sample, such that the sequencing library contains only a subset of the genomic sequence. As such, above described method is useful for the analysis of samples in a variety of diagnostic, drug discovery, and research applications. The above described method is useful for the analysis of biological samples. The term "biological sample," as used herein, refers to a sample obtained from an organism or from components (e.g., cells) of an organism. As the method described is a method for amplifying DNA, it may find particular use in areas where nucleic acids are only present in small amounts. For example, the described method may be useful for analysis of nucleic acids from a single cell, a small number of cells, a small fraction of a biopsy, or a fraction of a single cell. With sufficient amplification, the described method may be used to generate a sequencing library representing all, substantially all, a fraction of, or a selected fraction of the sequences present in a single cell or a small number of cells. The method may also be useful for analysis of cell-free DNA, such as cell-free fetal DNA, DNA from a liquid biopsy, DNA from exosomes, etc. Suitable cells for single cell analysis comprise human cells, mammalian cells, tumor cells, fetal cells, bacterial cells, yeast cells, plant cells, and the like.

In some embodiments, the nucleic acid sample may be made from a clinical sample, e.g., a sample from a patient suspected of having a disease or condition. The clinical sample may a bodily fluid or excretion listed below. In some embodiments, the clinical sample may be a tumor biopsy. Methods for extracting total DNA and RNA from various samples, e.g., clinical, forensic, and environmental samples, are well known in the art. Samples include, but are not limited to, skin swab, skin biopsy, saliva, tooth swab, tooth scrapping, cheek swabs, throat swab, sputum, endogastric sample, feces, urine, vaginal, cervical, endocervical, endometrial, nasal swab, lung, organ biopsy, and tissue biopsy. A sample can also be a bodily fluid. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, cfDNA (e.g., ctDNA) and urine. In particular embodiments, the sample may be a clinical sample, e.g., a sample collected from a patient. In certain cases, the DNA in these samples may be highly fragmented, e.g., to an average size in the range of 10 bp to 5 kb, e.g., 20 bp to 200 bp and in certain cases may be fragmented using the methods described herein. Methods for extracting total DNA from such samples are well known. Biological samples may also include sections of tissues such as frozen sections taken for histological purposes. The subject method also finds use in determining the identity of microbes in water, sewage, air samples, food products, including animals, vegetables, seeds, etc., soil samples, plant samples, microbial culture samples, cell culture samples, tissue culture samples, as well as in human medicine, veterinary medicine, agriculture, food science, bioterrorism, and industrial microbiology, etc.

In some embodiments the nucleic acids being analyzed may be derived from a single source (e.g., from different sites or a timecourse in a single subject), whereas in other embodiments, the nucleic acid sample may be a pool of nucleic acids extracted from a plurality of different sources (e.g., a pool of nucleic acids from different subjects), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Sample index sequences and molecular barcodes may allow the sequences from different sources to be distinguished after they are analyzed.

If the amplification products are sequenced, they may be sequenced by nanopore sequencing, for example using the Minion sequencer commercialized by Oxford Nanopore technologies, or other methods involving passing DNA or tags through a biological or solid-state nanopore. Alternatively, the sequencing may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, in some embodiments, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

Kits

Also provided by this disclosure are kits for practicing the subject method, as described above. In certain embodiments, the kit may comprise (a) a forward primer that hybridizes to a sequence in the bottom strand of a fragment in a sample; (b) a reverse primer, wherein the reverse primer has a hairpin structure comprising a loop, a stem and a 3' overhang of at least 8 nucleotides, wherein the 3' overhang hybridizes to a sequence in the top strand of the fragment (c) a polymerase, e.g., a non-strand displacing polymerase; and (d) a ligase. In some embodiments, the forward primer may a hairpin structure comprising a loop, a stem and a 3' overhang of at least 8 nucleotides, wherein the 3' overhang hybridizes to a sequence in the bottom strand of the fragment. The various components of the kit may be present in separate containers or certain compatible components may be precombined into a single container, as desired. In addition to the probe, the kit may contain any of the additional components used in the method described above, e.g., a buffer, etc.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EMBODIMENTS

Embodiment 1

A method for amplifying a nucleic acid, comprising:
(a) producing a reaction mix comprising:
i. a nucleic acid sample;
ii. a polymerase;
iii. nucleotides;
iv. a forward primer that hybridizes to a sequence in the bottom strand of a fragment in the sample; and v. a reverse primer, wherein the reverse primer has a hairpin structure comprising a loop, a stem and a 3' overhang of at least 8 nucleotides, wherein the 3' overhang hybridizes to a sequence in the top strand of the fragment; and (b) subjecting the reaction mix at least two rounds of denaturation, renaturation and primer extension conditions to extend the forward and reverse primers to produce an amplification product that contains: i. a double stranded region comprising a nick adjacent to the 5' end of the reverse primer, and ii. the loop of the first hairpin primer.

Embodiment 2

The method of embodiment 1, further comprising sealing the nick with a ligase.

Embodiment 3

The method of any prior embodiment wherein step (b) results in a concatemerized amplification product.

Embodiment 4

The method of any prior embodiment, wherein the forward primer is a linear primer.

Embodiment 5

The method of any of embodiments 1-3, wherein the forward primer has a hairpin structure comprising a loop, a stem and a 3' overhang of at least 8 nucleotides, wherein the 3' overhang hybridizes to a sequence in the bottom strand of the fragment, and wherein the amplification product further comprises the loop of the forward primer at the opposite end to loop of the reverse primer.

Embodiment 6

The method of embodiment 5, wherein the 5' end of the forward primer is not a 5' phosphate.

Embodiment 7

The method of embodiment 5, wherein the 5' end of the reverse primer is a 5' phosphate.

Embodiment 8

The method of any prior embodiment, wherein the forward primer is attached to a surface.

Embodiment 9

The method of embodiment 8, wherein step (b) results in an amplification product that is anchored to the surface.

Embodiment 10

The method of any prior embodiment, wherein a plurality of the strands of fragments in the sample are asymmetrically tagged with a 5' adaptor sequence and a 3' adaptor sequence, and the 3' overhang of the forward primer hybridizes to the 3' adaptor sequence and the 3' overhang of the reverse primer hybridizes to the complement of the 5' adaptor sequence.

Embodiment 11

The method of any prior embodiment, wherein step (b) is done by thermocycling.

Embodiment 12

The method of any prior embodiment, wherein the polymerase is a non-strand displacing polymerase Embodiment 13

The method of embodiment 11, wherein the polymerase is Pfu or a mutant thereof.

Embodiment 14

A primer system comprising: (a) a forward primer that hybridizes to a sequence in the bottom strand of a fragment in a sample; and (b) a reverse primer, wherein the reverse primer has a hairpin structure comprising a loop, a stem and a 3' overhang of at least 8 nucleotides, wherein the 3' overhang hybridizes to a sequence in the top strand of the fragment.

Embodiment 15

The primer system of embodiment 14, wherein the wherein the forward primer has a hairpin structure comprising a loop, a stem and a 3' overhang of at least 8 nucleotides, wherein the 3' overhang hybridizes to a sequence in the bottom strand of the fragment.

Embodiment 16

The primer system of embodiment 15, wherein the overhangs of the forward and reverse primers are not complementary to or the same as naturally occurring sequences from a cell.

Embodiment 17

The primer system of any of embodiments 14-16, wherein one primer has a 5' phosphate and the other has an unligatable 5' end.

Embodiment 18

The prime system of any of embodiments 14-17, wherein one primer linked to a solid support by its 5' end.

Embodiment 19

A kit comprising: (a) a forward primer that hybridizes to a sequence in the bottom strand of a fragment in a sample; (b) a reverse primer, wherein the reverse primer has a hairpin structure comprising a loop, a stem and a 3' overhang of at least 8 nucleotides, wherein the 3' overhang hybridizes to a sequence in the top strand of the fragment
(c) a polymerase; and
(d) a ligase;

Embodiment 20

The kit of embodiment 19, wherein the forward primer has a hairpin structure comprising a loop, a stem and a 3' overhang of at least 8 nucleotides, wherein the 3' overhang hybridizes to a sequence in the bottom strand of the fragment.

The invention claimed is:

1. A method for amplifying a nucleic acid, comprising:
(a) producing a reaction mix comprising:
i. a nucleic acid sample;
ii. a polymerase;
iii. nucleotides;
iv. a forward primer that hybridizes to a sequence in the bottom strand of a fragment in the sample; and
v. a reverse primer, wherein the reverse primer has a hairpin structure comprising a loop, a stem and a 3' overhang of at least 8 nucleotides, wherein the 3' overhang hybridizes to a sequence in the top strand of the fragment; and
(b) subjecting the reaction mix to at least two rounds of denaturation, renaturation and primer extension conditions to extend the forward and reverse primers to produce an amplification product that contains:
i. a double stranded region comprising a nick adjacent to the 5' end of the reverse primer, and
ii. the loop of the reverse primer.

2. The method of claim 1, further comprising sealing the nick with a ligase.

3. The method of claim 1, wherein step (b) results in a concatemerized amplification product.

4. The method of claim 1, wherein the forward primer is a linear primer.

5. The method of claim 1, wherein the forward primer has a hairpin structure comprising a loop, a stem and a 3' overhang of at least 8 nucleotides, wherein the 3' overhang hybridizes to a sequence in the bottom strand of the fragment, and wherein the amplification product further comprises the loop of the forward primer at the opposite end to loop of the reverse primer.

6. The method of claim 5, wherein the 5' end of the forward primer is not a 5' phosphate.

7. The method of claim 5, wherein the 5' end of the reverse primer is a 5' phosphate.

8. The method of claim 1, wherein the forward primer is attached to a surface.

9. The method of claim 8, wherein step (b) results in an amplification product that is anchored to the surface.

10. The method of claim 1, wherein the top strand of the fragment and the bottom strand of the fragment in the sample are asymmetrically tagged with a 5' adaptor sequence and a 3' adaptor sequence.

11. The method of claim 1, wherein step (b) is done by thermocycling.

12. The method of claim 1, wherein the polymerase is a non-strand displacing polymerase.

13. The method of claim 1, wherein the polymerase is Pfu or a mutant thereof.

* * * * *